United States Patent
Yan et al.

(10) Patent No.: US 11,280,774 B2
(45) Date of Patent: Mar. 22, 2022

(54) ENHANCED LOCATION DETECTION USING SENSORS INTEGRATED IN ELECTRONIC DEVICES

(71) Applicant: Apple Inc., Cupertino, CA (US)

(72) Inventors: Miaolei Yan, Santa Clara, CA (US); Roberto M. Ribeiro, San Jose, CA (US); Richard Yeh, Los Altos, CA (US)

(73) Assignee: Apple Inc., Cupertino, CA (US)

(*) Notice: Subject to any disclaimer, the term of this patent is extended or adjusted under 35 U.S.C. 154(b) by 430 days.

(21) Appl. No.: 16/115,478

(22) Filed: Aug. 28, 2018

(65) Prior Publication Data

US 2019/0120806 A1 Apr. 25, 2019

Related U.S. Application Data

(60) Provisional application No. 62/552,311, filed on Aug. 30, 2017.

(51) Int. Cl.
    *G01N 33/00* (2006.01)
    *G01N 35/00* (2006.01)
    *G01N 1/02* (2006.01)

(52) U.S. Cl.
CPC ....... *G01N 33/0031* (2013.01); *G01N 33/004* (2013.01); *G01N 33/0039* (2013.01); *G01N 33/0062* (2013.01); *G01N 33/0073* (2013.01); *G01N 33/0037* (2013.01); *G01N 33/0047* (2013.01); *G01N 35/00871* (2013.01); *G01N 2001/021* (2013.01); *G01N 2033/0068* (2013.01); *G01N 2035/00881* (2013.01)

(58) Field of Classification Search
CPC .......... G01N 33/0031; G01N 33/0073; G01N 33/0039; G01N 33/004; G01N 33/0062; G01N 2001/021; G01N 2001/2035; G01N 2001/00881; G01N 35/00871; G01N 33/0047; G01N 33/0037; G01N 2033/0068; Y02A 50/20
See application file for complete search history.

(56) References Cited

U.S. PATENT DOCUMENTS

| | | | | |
|---|---|---|---|---|
| 9,182,751 | B1* | 11/2015 | Reeder | G01N 33/004 |
| 2012/0192622 | A1* | 8/2012 | Lane | G01C 21/005 |
| | | | | 73/29.02 |
| 2015/0073741 | A1* | 3/2015 | Wuest | G01B 11/14 |
| | | | | 702/104 |
| 2017/0328591 | A1* | 11/2017 | Kelly | F24F 3/1603 |
| 2018/0017513 | A1* | 1/2018 | Le Neel | G01N 27/128 |
| 2018/0370538 | A1* | 12/2018 | Docker | B60W 40/105 |
| 2019/0035249 | A1* | 1/2019 | Mou | G08B 21/12 |

* cited by examiner

*Primary Examiner* — Peter J Macchiarolo
*Assistant Examiner* — John M Royston
(74) *Attorney, Agent, or Firm* — Morgan, Lewis & Bockius LLP

(57) ABSTRACT

A portable communication device includes one or more miniature sensors to sense one or more environmental gases. A processor is coupled to the miniature sensors and is configured to enhance location detection by determining a sensor signal transition. The sensor signal transition is caused by subsequent exposures of at least one of the miniature sensors to environmental gases of a first air composition and a second air composition. The first air composition and the second air composition are respectively associated with a first location and a second location.

21 Claims, 6 Drawing Sheets

ENHANCED LOCATION DETECTION USING SENSORS INTEGRATED IN ELECTRONIC DEVICES

CROSS-REFERENCE TO RELATED APPLICATIONS

This application claims the benefit of priority under 35 U.S.C. § 119 from U.S. Provisional Patent Application 62/552,311 filed Aug. 30, 2017, which is incorporated herein by reference in its entirety.

TECHNICAL FIELD

The present description relates generally to location detection, and more particularly, to enhanced location detection using gas and particulate matter sensors integrated in electronic devices.

BACKGROUND

Many mobile electronic platforms including portable communication devices such as smart phones and smart watches are enabled to provide location based contextual awareness. Indoor-outdoor detection is an enhanced location detection, which may be useful in a number of applications, for example, environmental and health monitoring and smart home applications. Current technologies for outdoor detection are mostly based on GPS signals (e.g., geo-fencing). Other technologies such as cellular signal strength, Wi-Fi fingerprinting, Bluetooth connectivity, beacon technology, near-field communications (NFC) or other near field radios and/or signal fusion may be used to achieve indoor detection. These technologies typically require the pretense of certain infrastructure to function, such as cell phone towers and or Wi-Fi routers.

Indoor and outdoor environments typically differ by their air compositions and concentrations, which can be captured by gas sensors and potentially used for indoor-outdoor (I-O) detection. Single gas composition and/or concentration or multi-gas identification could be used. One particular example is tropospheric ozone ($O_3$) gas, the ground level of which is usually formed outdoors, by photochemical and chemical reactions between nitrogen oxides (NOx) and volatile organic compounds (VOCs) in the presence of sunlight. Ozone naturally breaks down in indoor environments, especially on surfaces where unsaturated carbon-carbon bonds are present, which results in a lower ozone concentration indoors than outdoors.

BRIEF DESCRIPTION OF THE DRAWINGS

Certain features of the subject technology are set forth in the appended claims. However, for purposes of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without one or more of the specific details. In some instances, structures and components are shown in block diagram form in order to avoid obscuring the concepts of the subject technology.

In one or more aspects, the subject technology is directed to enhanced location detection using gas and/or particulate matter sensors integrated in electronic devices. It is understood that integration of miniature gas and/or particulate matter sensors into consumer electronic platforms is valuable as it could enable new features such as environmental, health monitoring and other various features. In particular, integration of one or more miniature sensors with a consumer electronic platform such as a portable communication device can enhance location detection accuracy of the device. This enables the device to more accurately distinguish a transition between indoor and outdoor based on detected transition in concentration of a signature gas, for example, ozone ($O_3$) or carbon dioxide ($CO_2$) or based on composition difference of indoor and outdoor gases or particulate matter. A processor coupled to the miniature sensors can determine a sensor signal transition when a user of the device moves the device from indoor to outdoor or from one location in a building to another location. In one or more implementations, the miniature sensors of the subject technology can be used in a number of applications including barometer improvement, smart home integration, device power saving and context awareness applications. For example, the processor can enable use of the miniature sensors in such applications by controlling sensor operations and performing suitable processing of the corresponding measured signals.

Figure 1:
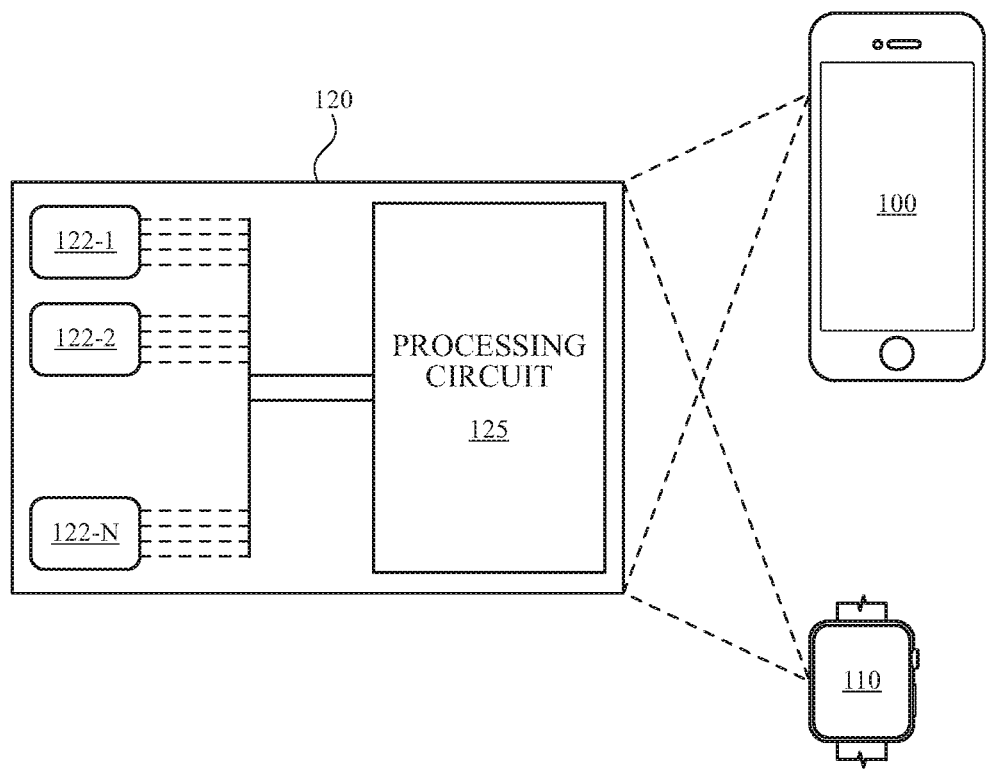
FIG. 1 is a schematic diagram illustrating an example of portable communication devices with enhanced location detection capability, in accordance with one or more aspects of the subject technology.

FIG. 1 is a schematic diagram illustrating an example of portable communication devices 100 and 110 with enhanced location detection capability, in accordance with one or more aspects of the subject technology. The portable communication devices 100 and 110 can be a smart phone and a smart watch as shown in FIG. 1 and discussed herein, although examples of portable communication devices that can include the features of the subject technology are not limited to the smart phone and a smart watch and can be any other portable communication device such as a personal digital assistant (PDA). In some aspects, the features of the subject technology can be implemented in any consumer electronic platform or as a stand-alone device.

The portable communication devices 100 and 110 include one or more sensors 122 (e.g., 122-1, 122-2 . . . 122-N) and a processing circuit 125. The sensors 122 are miniature sensors that can be readily integrated with a host device such as the portable communication devices 100 and 110. The miniature sensors may be gas sensors based on one of a number of gas sensing technologies including optical, electrochemical and chemo-resistive gas sensing technologies. In some implementations, one or more of the sensors 122 can be ozone ($O_3$) sensors, carbon dioxide ($CO_2$) sensors or sensors of other gases that may be associated with various neighboring locations. In some implementations, the sensor 122 can be a multi-pixel gas sensor, for example formed of an array of gas sensors, each of which can be sensitive to a particular gas. In some embodiments, the sensors 122 can be particulate matter sensors.

The processing circuit 125 is capable of processing data received from the sensors 122. In some aspects, the processing circuit 125 may provide DC bias and an AC voltage for the operation of the sensor 122. The processing circuit 125 may include suitable analog and digital circuitry that preprocesses the data received from the sensors 122. In one or more aspects, the processing circuit 125 can include one or more filters (e.g., a median filter) that can remove noise and smooth the raw data. The median filter can be implemented digitally and when applied to the data from the sensors 122 can improve edge detection when data transitions are studied. At least some part of the functionalities of the processing circuit 125 (e.g., after the preprocessing of the raw sensors data) can be performed by a central processor of the host device (e.g., the portable communication devices 100 and 110). The processing circuit 125 may be in communication with other components and modules of the host device for example a memory (e.g., volatile or non-volatile) of the host device that can store or buffer at least portions of the sensor data. In some aspects, certain signals such as a Bluetooth signal, for example, from detection of a car connection or a home speaker connection can help improve indoor-outdoor (I-O) location accuracy. Signals from other sensors and components of the host device such ambient light sensors (ALSs), proximity sensors, ultraviolet (UV) sensors, barometers, accelerometer, gyroscope, speakers, or other component of the host device can be used by the processor to enhance the I-O detection of the host device.

For example, the ALS and proximity sensor signals can, for example, help determine if the sensor (e.g., 122) is occluded by clothing fabrics or pockets and/or bags, which can impact gas sensor accuracy, UV sensors can help improve accuracy of I-O detection, and barometers can be used to detect if the gas sensor and its port is occluded by water. The host device may use signals from an accelerometer and a gyroscope to detect user motion to reject false I-O transition signals, or use a haptic engine or a speaker to pump air to the gas sensor for active sampling.

Figure 2:
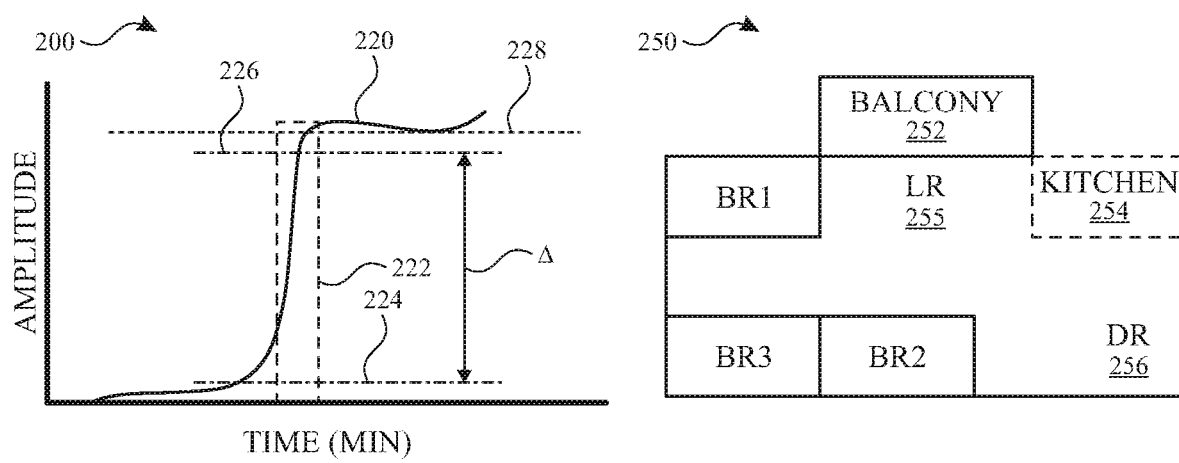
FIG. 2 shows a chart and a schematic diagram illustrating an example sensor signal transition used to enhance location detection, in accordance with one or more aspects of the subject technology.

FIG. 2 shows a chart and a schematic diagram illustrating an example sensor signal transition 222 used to enhance location detection, in accordance with one or more aspects of the subject technology. The raw data from sensors 122 of FIG. 1, after processing by the processing circuit 125 of FIG. 1 is converted to a sensor signal 220 that may show a sensor signal transition 222. The sensor signal transition 222 can be due to a change of concentration of a signature gas or due to a change in air composition that the sensor is exposed to. For example, if the sensor is an ozone sensor and the user of the host device (e.g., 100 or 110 of FIG. 1) moves the host device from indoor (e.g., a space in the building 250, such as the living room (LR) 255) to outdoor (e.g., balcony 252), the ozone signal (e.g., 220) shows the sensor signal transition 222, which is an indication of a change in concentration of ozone gas. It is understood that the concentration of the ozone gas is significantly higher outdoor than indoor. This is because the ground level ozone is usually formed outdoors (e.g., by reactions between sunlight, nitrogen oxides, and volatile organic compounds), and naturally breaks down in indoor environments. This results in a higher $O_3$ concentration outdoors than indoors.

In some aspects, other gases such as carbon dioxide can be a signature gas for detecting indoor-outdoor (I-O) transition or transition from a room with more people (e.g., a LR 255 or a dining room (DR) 256 to a bedroom (e.g., BR1). In one or more aspects, the change in air composition in a first location (e.g., kitchen 254) may be different from the air composition in a bedroom (e.g., BR1, BR2, or BR3). This can result in a transition in sensors response when data from a number of sensors 122 are analyzed. For example, air composition percentages of at least one of the different gases that different sensors 122 are sensitive to a change in a location of the host device from a first location to a second location, which can cause a transition in a combined sensor signals. There may be different ways that signals from multiple sensors 122 can be combined to result in a stronger signal transition. The transition may be associated with a change Δ in the signal amplitude, for example, when the amplitude changes from a first level 224 (e.g., 10% of a highest amplitude represented by line 228) to a second level 226 (e.g., 90% of the highest amplitude). In some implementations, the I-O transition detection can be based on concentration of particulate matters, which can be higher outdoors as compared to indoors.

The indoor-outdoor (I-O) transition detection can enable new features and/or improvement of performance of existing features in the host device. For example, improvement in barometer performances can be achieved by identifying I-O transition and using the I-O transition information to reject portions of a signal (e.g., pressure signal) as noise or false positive, as opposed to being interpreted as a change in altitude (e.g., flight of stairs). The host device may benefit from the I-O transition identification in a number of other ways. For instance, in a health-related application on a host device such as a smart watch or smart phone, the relevance of possible workout options can be increased by knowing whether the user of the host device is indoors or outdoors. As another example, the power saving mode of a host device can be enabled when it is detected that the user is outdoors (e.g., by turning off Wi-Fi). Further, the user can be alerted to enable air quality measurement to contribute to crowd-sourcing of air quality data, when it is detected that the user is outdoors. The I-O transition identification feature may also enable features such as cumulative indoors/outdoors time measurement, providing additional confidence to home automation and home kit integrations (e.g., by reducing level of HVAC when detecting a window is open), enhancing location sensing, for example, to find the host device, improving indoor navigation (e.g., between kitchen, bedroom, garage, balcony, etc.) and enhancing existing host device features (e.g., "remind me when" feature) based on location (e.g., I-O) knowledge.

Figure 3:
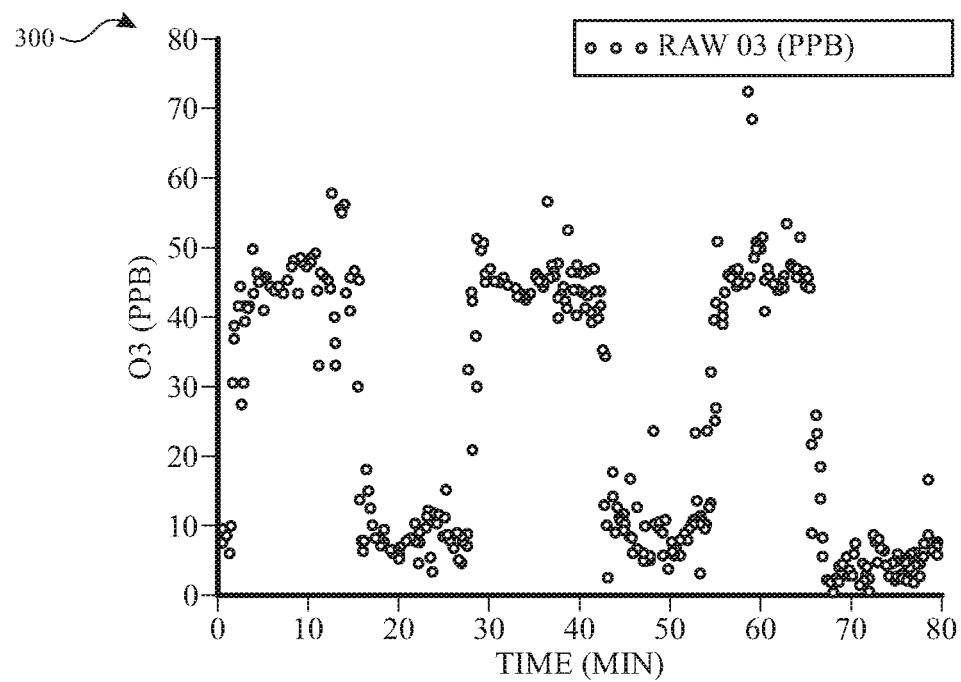
FIG. 3 shows charts illustrating examples of raw and filtered sensor data showing signal transitions with location change, in accordance with one or more aspects of the subject technology.
Figure 3:
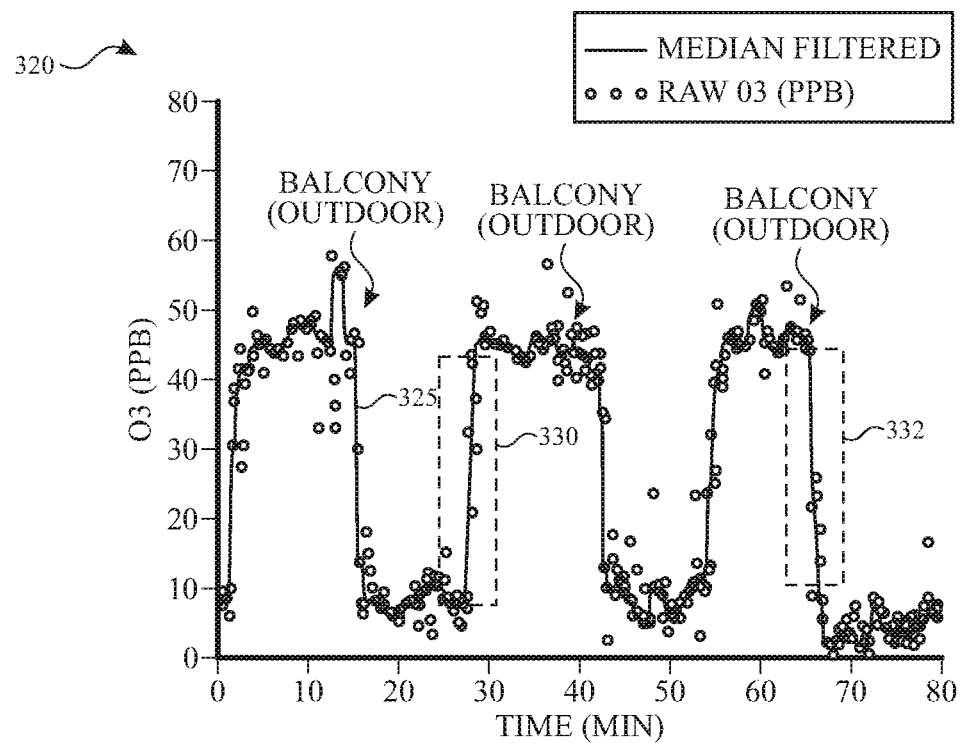

FIG. 3 shows charts illustrating example of raw sensor data 300 and filtered sensor data 320 showing signal transitions with location change, in accordance with one or more aspects of the subject technology. The example raw sensor data 300 indicate variation of concentration of a signature gas (e.g., ozone or particulate matter) over time as the host device is placed alternately in a first place (e.g., balcony 252 of FIG. 2) and a second place (e.g., a closed space such as BR1 of FIG. 2 with windows closed). The measured data rate can be a few data points per minute (e.g., 1 data point per 10 seconds). The sensor raw data may include data corresponding to a single gas species, multiple gas species or particulate matter.

The processing circuit 125 of FIG. 1 can process the raw sensor data, for example, by filtering (e.g., using a median filter or other filters) the raw sensor data 300 to generate a filtered (e.g., smooth) sensor data 325 shown with lines (rather than data points). The processing circuit 125 can further determine the sensor signal transitions 330 and/or 332 based on an analysis of the filtered sensor data 320. The sensor signal transitions 330 can be associated with an I-O transition and the sensor signal transitions 332 can an indication of an outdoor-indoor (O-I) transition.

Figure 4:
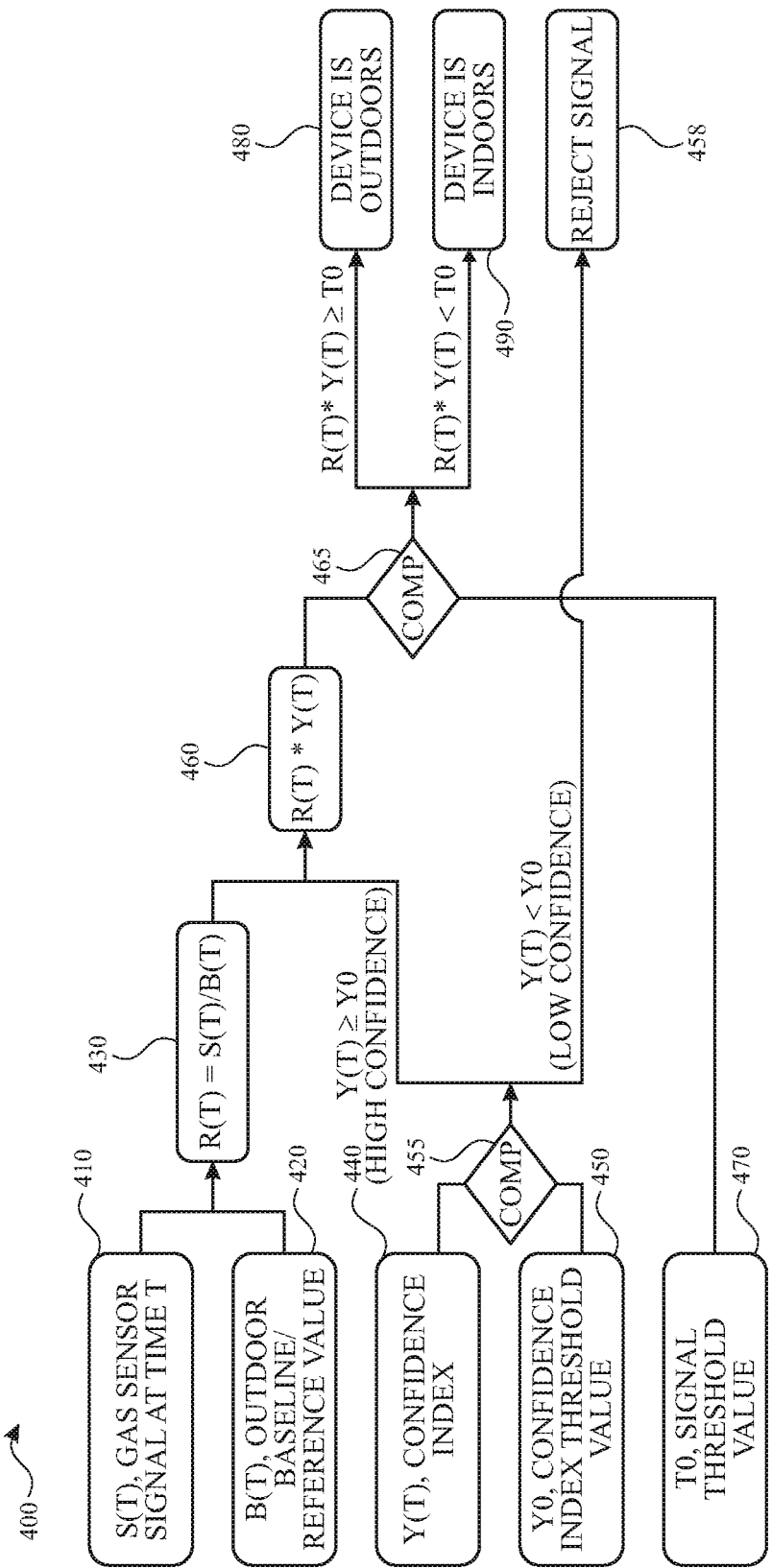
FIG. 4 is a flow diagram illustrating an example method of indoor-outdoor transition detection based on sensor data and a baseline reference, in accordance with one or more aspects of the subject technology.

FIG. 4 is a flow diagram illustrating an example method 400 of I-O transition detection based on sensor data and a baseline reference, in accordance with one or more aspects of the subject technology. The method 400 describes a method to detect whether the user is indoors or outdoors, by comparing the gas sensor signal with a baseline or reference value extracted from another source, such as air quality monitoring stations (EPA stations) or crowdsourced air quality data. The method 400 begins with an operation block 410, where the gas sensor data S(t) (e.g., 325 of FIG. 2) collected over time (t) by the gas sensors (e.g., 122 of FIG. 1) are analyzed. Further, at an operation block 420, outdoor baseline or reference value is prepared based on the other source. At an operation block 430, a ratio R(t)=S(t)/H(t) is determined. Other sensor data (e.g., location from a global positioning system (GPS), device occlusion status from a proximity sensor, motion from inertial measurement units (IMU)) are collected and used to determine a confidence index Y(t), at an operation block 440. The confidence index Y(t) is compared, at a control operation block 455, with Y0, a confidence index threshold value established at operation block 450. If Y(t) is less than Y0, data is automatically rejected, at operation block 458, due to low confidence. If Y(t) is greater than or equal to Y0, the confidence index Y(t) is multiplied, at an operation block 460, by the ratio R(t) to generate Y(t)*R(t). At an operation block 470, a predefined signal threshold value T0 is established. In some implementations, the value of T0 can be optimized. In some aspects, the value of about 3 or greater can be used for T0. At a decision block 465, a value of Y(t)*R(t) is compared with the predefined threshold value T0. If the value of Y(t)*R(t) is larger than or equal to T0, at operation block 480, it is established that the device is outdoors. Otherwise, if the value of Y(t)*R(t) is smaller than T0, at operation block 490, it is established that the device is indoors.

Figure 5:
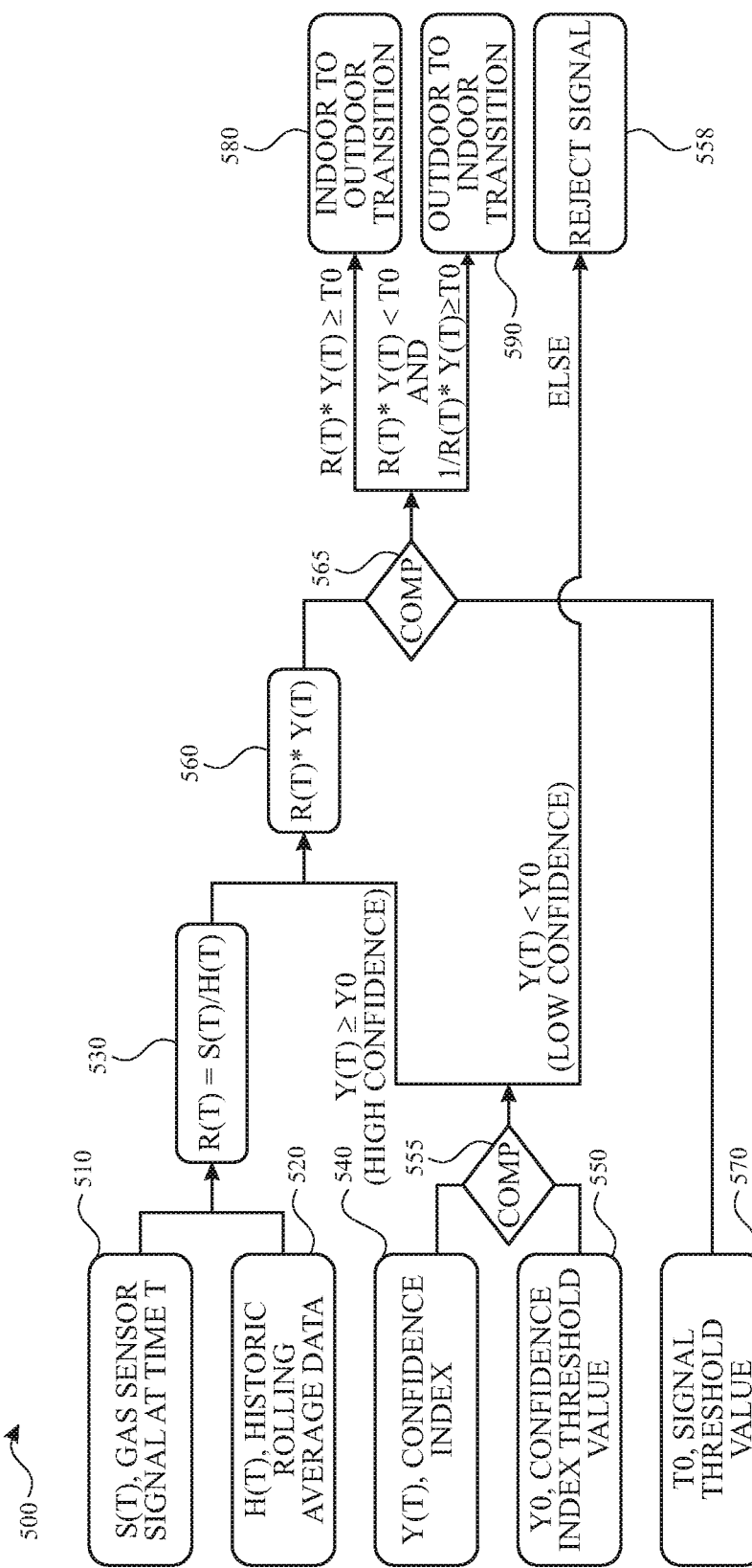
FIG. 5 is a flow diagram illustrating an example method of I-O transition detection based on sensor data, in accordance with one or more aspects of the subject technology.

FIG. 5 is a flow diagram illustrating an example method 500 of I-O transition detection based on sensor data, in accordance with one or more aspects of the subject technology. The method 500 begins with an operation block 510, where the gas sensor data S(t) (e.g., 325 of FIG. 2) collected over time (t) by the gas sensors (e.g., 122 of FIG. 1) are analyzed. Further, at an operation block 520, historic rolling average data H(t) related to the same sensor is prepared based on stored data. At an operation block 530, a ratio R(t)=S(t)/H(t) is determined. Other sensor data (e.g., location from a global positioning system (GPS), device occlusion status from a proximity sensor, motion from inertial measurement units (IMU)) are collected and used to determine a confidence index Y(t), at an operation block 550. The confidence index Y(t) is compared, at a control operation block 555, with Y0, a confidence index threshold value established at operation block 550. If Y(t) is less than Y0, data is automatically rejected (558) due to low confidence. If Y(t) is greater than or equal to Y0, the confidence index Y(t) is multiplied, at an operation block 560, by the ratio R(t) to generate Y(t)*R(t). At an operation block 570, a predefined signal threshold value T0 is established. In some implementations, the value of T0 can be optimized. In some aspects, the value of about 3 or greater can be used for T0. At a decision block 565, a value of Y(t)*R(t) is compared with the predefined threshold value T0. If the value of Y(t)*R(t) is larger than or equal to T0, at operation block 580, it is established that the transition signal (e.g., 330 of FIG. 3) corresponds to an indoor-to-outdoor transition. Otherwise, if the value of Y(t)*R(t) is smaller than T0 and in the meantime the value of Y(t)/R(t) is larger than or equal to T0, at operation block 590, it is established that the transition signal corresponds to an outdoor-to-indoor transition. In all other scenarios, either the signal does not correspond to an I-O transition or the confidence is low, at operation block 558, the signal is rejected.

Figure 6:
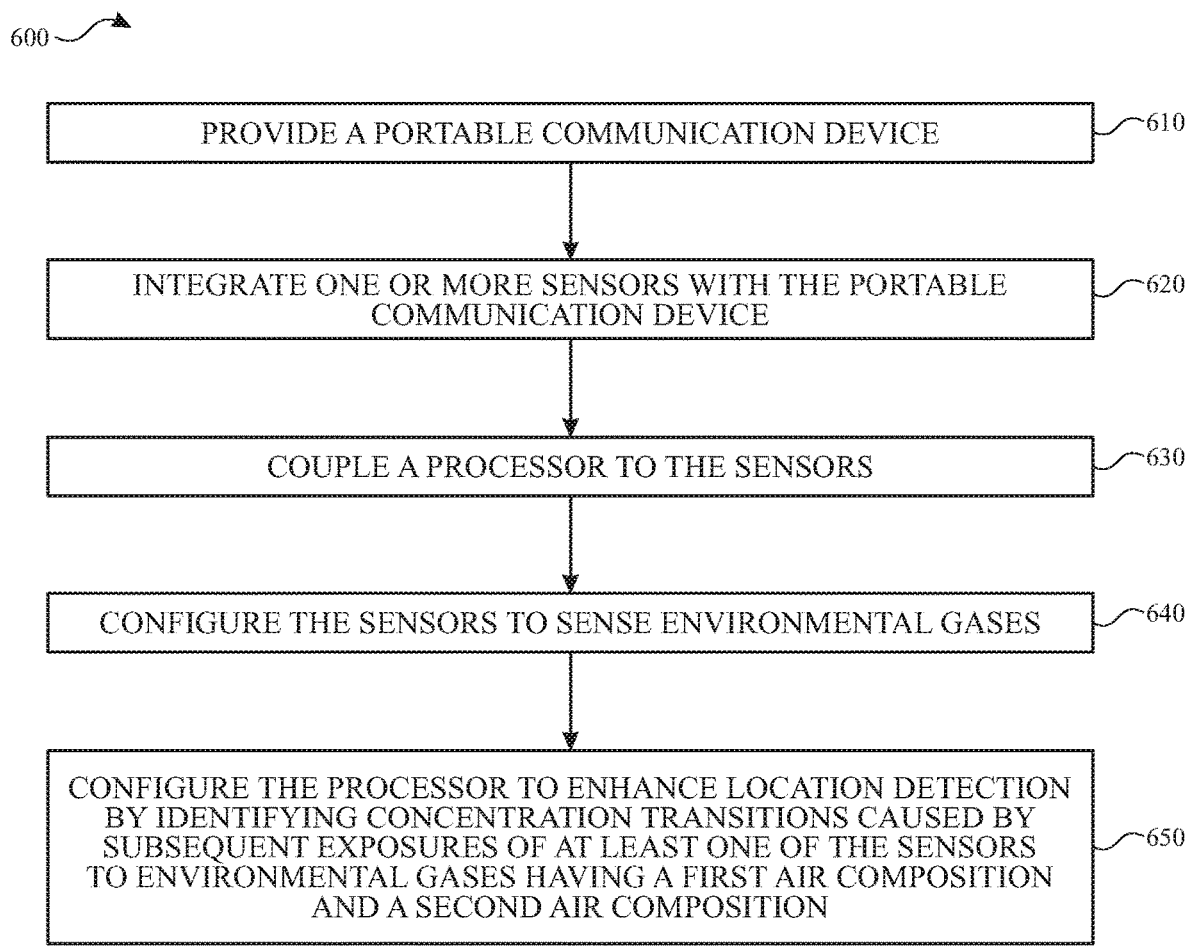
FIG. 6 is a flow diagram illustrating an example method of providing a portable communication device with enhanced location detection capability, in accordance with one or more aspects of the subject technology.

FIG. 6 is a flow diagram illustrating an example method 600 of providing a portable communication device with enhanced location detection capability, in accordance with one or more aspects of the subject technology. The method begins with providing a portable communication device (e.g., 100 or 110 of FIG. 1) (610). One or more sensors (e.g., 122 of FIG. 1) are integrated with the portable communication device (620). A processor (e.g., 125 of FIG. 1) is coupled to the one or more sensors (630). The sensors are configured to sense one or more environmental gases (e.g., ozone, particulate matter or carbon dioxide) (640). The processor is configured to enhance location detection by identifying concentration transitions (e.g., 222 of FIG. 2) caused by subsequent exposures of at least one of the one or more sensors to environmental gases having a first air composition and a second air composition (650).

Figure 7:
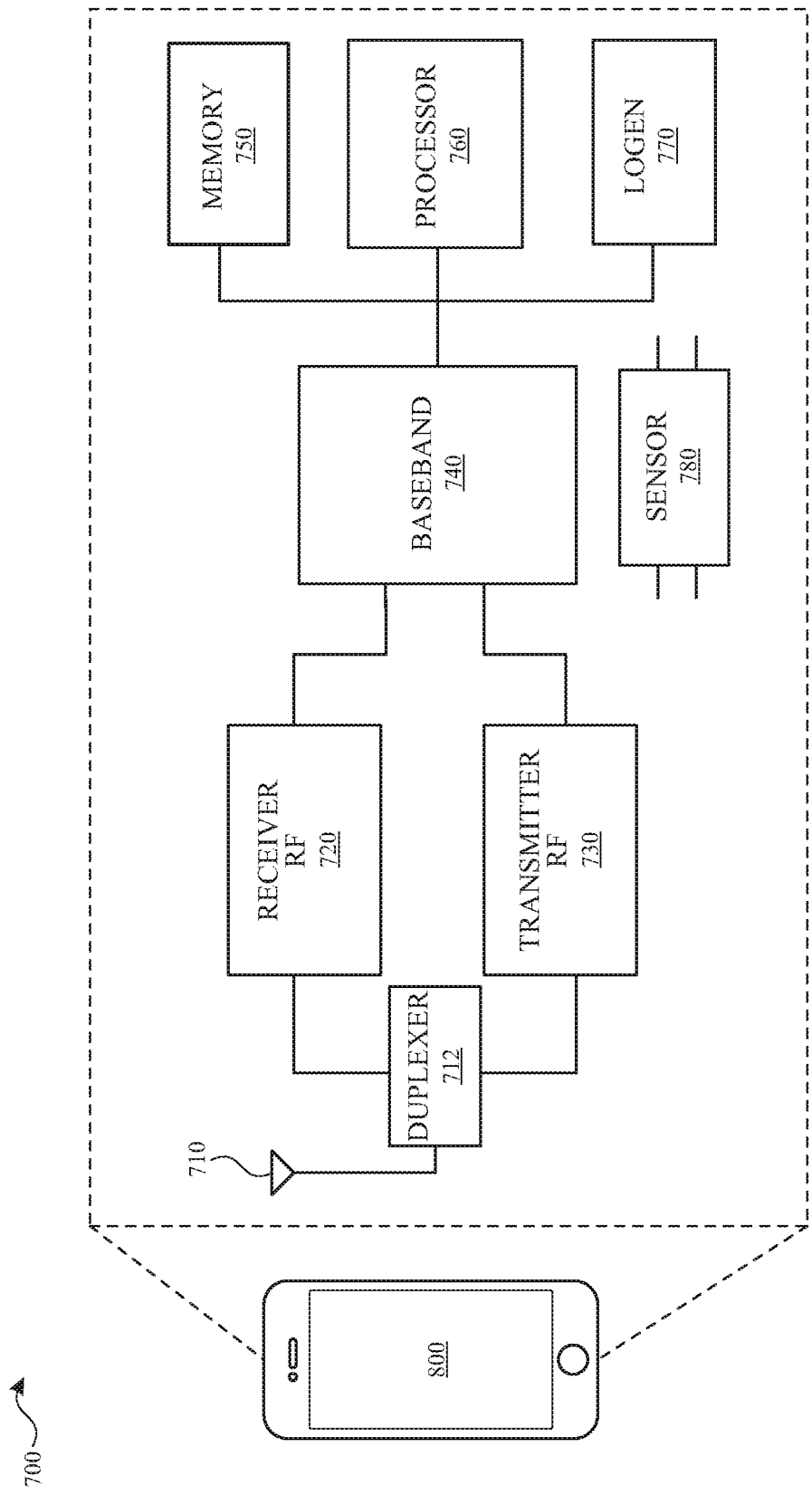
FIG. 7 is a block diagram illustrating an example wireless communication device, within which one or more sensors of the subject technology can be integrated.

FIG. 7 is a block diagram illustrating an example wireless communication device 700, within which one or more sensors of the subject technology can be integrated. The wireless communication device 700 may comprise a radio-frequency (RF) antenna 710, a duplexer 712, a receiver 720, a transmitter 730, a baseband processing module 740, a memory 750, a processor 760, a local oscillator generator (LOGEN) 770 and one or more sensors 780. In various embodiments of the subject technology, one or more of the blocks represented in FIG. 7 may be integrated on one or more semiconductor substrates. For example, the blocks 720-770 may be realized in a single chip or a single system on a chip, or may be realized in a multi-chip chipset.

The receiver 720 may comprise suitable logic circuitry and/or code that may be operable to receive and process signals from the RF antenna 710. The receiver 720 may, for example, be operable to amplify and/or down-convert received wireless signals. In various embodiments of the subject technology, the receiver 720 may be operable to cancel noise in received signals and may be linear over a wide range of frequencies. In this manner, the receiver 720 may be suitable for receiving signals in accordance with a variety of wireless standards, Wi-Fi, WiMAX, Bluetooth, and various cellular standards. In various embodiments of the subject technology, the receiver 720 may not require any SAW filters and few or no off-chip discrete components such as large capacitors and inductors.

The transmitter 730 may comprise suitable logic circuitry and/or code that may be operable to process and transmit signals from the RF antenna 710. The transmitter 730 may, for example, be operable to up-convert baseband signals to RF signals and amplify RF signals. In various embodiments of the subject technology, the transmitter 730 may be operable to up-convert and amplify baseband signals processed in accordance with a variety of wireless standards. Examples of such standards may include Wi-Fi, WiMAX, Bluetooth, and various cellular standards. In various embodiments of the subject technology, the transmitter 730 may be operable to provide signals for further amplification by one or more power amplifiers.

The duplexer 712 may provide isolation in the transmit band to avoid saturation of the receiver 720 or damaging parts of the receiver 720, and to relax one or more design requirements of the receiver 720. Furthermore, the duplexer 712 may attenuate the noise in the receive band. The duplexer may be operable in multiple frequency bands of various wireless standards.

The baseband processing module 740 may comprise suitable logic, circuitry, interfaces, and/or code that may be operable to perform processing of baseband signals. The baseband processing module 740 may, for example, analyze received signals and generate control and/or feedback signals for configuring various components of the wireless communication device 700, such as the receiver 720. The baseband processing module 740 may be operable to encode, decode, transcode, modulate, demodulate, encrypt, decrypt, scramble, descramble, and/or otherwise process data in accordance with one or more wireless standards.

The processor 760 may comprise suitable logic, circuitry, and/or code that may enable processing data and/or controlling operations of the wireless communication device 700. In this regard, the processor 760 may be enabled to provide control signals to various other portions of the wireless communication device 700. The processor 760 may also control transfers of data between various portions of the wireless communication device 700. Additionally, the processor 760 may enable implementation of an operating system or otherwise execute code to manage operations of the wireless communication device 700. In some aspects, the processor 760 may partially or entirely perform operations described in the methods 400 and 500 of FIGS. 4 and 5.

The memory 750 may comprise suitable logic, circuitry, and/or code that may enable storage of various types of information such as received data, generated data, code, and/or configuration information. The memory 750 may comprise, for example, RAM, ROM, flash, and/or magnetic storage. In various embodiment of the subject technology, information stored in the memory 750 may be utilized for configuring the receiver 720 and/or the baseband processing module 740. In some embodiments, the memory 750 may store sensor data, for example, collected from sensors 780 for the processor 760 to identify indoor-outdoor or other location changes based on, for example, sensor signal transitions as shown in FIG. 2.

The local oscillator generator (LOGEN) 770 may comprise suitable logic, circuitry, interfaces, and/or code that may be operable to generate one or more oscillating signals of one or more frequencies. The LOGEN 770 may be operable to generate digital and/or analog signals. In this manner, the LOGEN 770 may be operable to generate one or more clock signals and/or sinusoidal signals. Characteristics of the oscillating signals such as the frequency and duty cycle may be determined based on one or more control signals from, for example, the processor 760 and/or the baseband processing module 740.

In operation, the processor 760 may configure the various components of the wireless communication device 700 based on a wireless standard according to which it is desired to receive signals. Wireless signals may be received via the RF antenna 710 and amplified and down-converted by the receiver 720. The baseband processing module 740 may perform noise estimation and/or noise cancellation, decoding, and/or demodulation of the baseband signals. In this manner, information in the received signal may be recovered and utilized appropriately. For example, the information may be audio and/or video to be presented to a user of the wireless communication device, data to be stored to the memory 750, and/or information affecting and/or enabling operation of the wireless communication device 700. The baseband processing module 740 may modulate, encode, and perform other processing on audio, video, and/or control signals to be transmitted by the transmitter 730 in accordance with various wireless standards.

The one or more sensors 780 may include the gas and particulate matter sensors of the subject technology (e.g., 122 of FIG. 1) that can detect a signature gas such as ozone ($O_3$), carbon dioxide ($CO_2$), and/or particulate matter as described above. The miniature gas sensors of the subject technology can be readily integrated into the communication device 700, in particular when the communication device 700 is a smart mobile phone or a smart watch.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

The word "example" is used herein to mean "serving as an example or illustration." Any aspect or design described herein as "example" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A portable communication device, the device comprising:
   one or more miniature sensors configured to sense one or more environmental gases in a location; and
   a processor coupled to the one or more miniature sensors and configured to provide an enhanced position detection accuracy within the location by determining a sensor signal transition when at least one of the one or more miniature sensors is moved within the location between a first position having a first air composition and a second position having a second air composition, wherein the location comprises a building.

2. The device of claim 1, wherein the first air composition is associated with an indoor position and the second air composition is associated with an outdoor position.

3. The device of claim 2, wherein the first air composition and the second air composition include different concentration levels of a signature gas, wherein the one or more environmental gases includes particulate matter, and wherein the first air composition and the second air composition include different concentration levels of particulate matter.

4. The device of claim 3, wherein the signature gas comprises ozone ($O_3$), and wherein a first concentration level of the signature gas in the first position is different from a second concentration level of the signature gas in the second position by at least a threshold value.

5. The device of claim 3, wherein the signature gas comprises carbon dioxide ($CO_2$), and wherein the first position and the second position are two different spaces of a building.

6. The device of claim 1, wherein the processor is configured to determine the sensor signal transition based on an analysis of sensor data collected over time, and wherein the sensor data comprises data corresponding to a single gas species or multiple gas species.

7. The device of claim 1, wherein the processor is configured to determine a confidence index (CI) based on sensor data collected over time.

8. The device of claim 1, wherein the processor is configured to determine the sensor signal transition corresponding to a change in a position of the device between the first position and the second position.

9. The device of claim 1, wherein the first position and the second position are different spaces of a smart home, and wherein the device is in network communication with other devices of the smart home.

10. The device of claim 1, wherein the miniature sensor comprises a miniature gas sensor.

11. The device of claim 10, wherein the miniature gas sensor is based on at least one of a list of gas sensing technologies including optical, electrochemical and chemi-resistive gas sensing technologies, and wherein chemi-resistive-based miniature gas sensors include metal-oxide semiconductors-based, graphene-based or carbon nanotubes-based gas sensors.

12. A device comprising:
   one or more miniature sensors configured to measure concentrations of one or more environmental gases in a location; and
   a processor configured to receive and perform processing of signals received from the one or more miniature sensors,
   wherein:
   the signals comprise gas concentration versus time signals,
   the processing of signals includes:
   identifying a signal indicative of a position transition within the location when at least one of the one or more miniature sensors is moved between a first position having a first air composition and a second position having a second air composition, and
   enhancing a position detection accuracy by using the identified signal indicative of the position transition, wherein the location comprises a building.

13. The device of claim 12, wherein the one or more environmental gases include particulate matter, wherein the first position and the second position comprise indoor and outdoor positions, and wherein the first air composition and the second air composition are associated with at least one of different concentration levels of a signature gas or different concentration levels of the particulate matter.

14. The device of claim 13, wherein the signature gas comprises ozone ($O_3$), and wherein the different concentration levels of the signature gas are different by at least a threshold value.

15. The device of claim 13, wherein the signature gas comprises carbon dioxide ($CO_2$), and wherein the building comprises a smart home.

16. The device of claim 12, wherein the processor is configured to identify the signal indicative of the position transition based on analysis of sensor data collected over time, and wherein the sensor data comprises data corresponding to a single gas species or multiple gas species.

17. The device of claim 12, wherein the processor is configured to identify the signal indicative of the position transition corresponding to a change in a position of the device between the first position and the second position of a building, wherein the building comprises a smart home equipped with multiple sensors in network communication with the device.

18. The device of claim 12, wherein the processor is configured to enable use of the one or more miniature sensors in a plurality of applications including barometer improvement, smart home integration, device power saving and context awareness applications.

19. A system comprising:
   a portable communication device;
   one or more sensors integrated with the portable communication device; and a processor coupled to the one or more sensors,
wherein:
the one or more sensors are configured to sense one or more environmental gases in a location, and
the processor is configured to:
determine a sensor signal transition when at least one of the one or more miniature sensors is moved within the location between a first position having a first air composition and a second position having a second air composition' and
enhance a position detection accuracy within the location by using the identified signal indicative of the position transition, wherein the location comprises a building.

20. The system of claim 18, wherein the one or more environmental gases include particulate matter, wherein the first air composition and the second air composition include different concentration levels of a signature gas and are associated with a first position and a second position, and wherein the first position and a second position comprise indoor and outdoor positions and the signature gas comprises ozone ($O_3$) gas or the particulate matter.

21. The device of claim 6, wherein the sensor data includes data from a global positioning system (GPS), device occlusion data from a proximity sensor and motion data from one or more inertial measurement units (IMUs).

* * * * *